US00PP18051P2

(12) United States Plant Patent
Hanes

(10) Patent No.: US PP18,051 P2
(45) Date of Patent: Sep. 18, 2007

(54) ***PETUNIA* PLANT NAMED 'JAM PLUMEIN'**

(50) Latin Name: ***Petunia* sp.**
Varietal Denomination: Jam Plumein

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/369,369

(22) Filed: Mar. 7, 2006

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—June Hwu
(74) *Attorney, Agent, or Firm*—Jondle & Associates, P.C.

(57) ABSTRACT

A new *petunia* plant particularly distinguished by large, purple to purple-pink flowers with strong dark veins, medium-green foliage with elliptical leaves, a medium, round, bushy, moderately tight plant habit with moderately vigorous growth, an initially low spreading to later decumbent or trailing plant habit with an early to medium and continuous flowering response, is disclosed.

1 Drawing Sheet

Genus and species: *Petunia* sp.
Variety denomination: 'Jam Plumein'.

BACKGROUND OF THE NEW PLANT

The present invention comprises a new and distinct cultivar of *petunia,* botanically known as a *Petunia* sp., and hereinafter referred to by the cultivar name 'Jam Plumein'. The new cultivar originated from a hybridization made in February 2003 in Gilroy, Calif. The female parent was 'Jam Bluintwo', a blue-flowered proprietary *petunia* plant (U.S. Plant patent application Ser. No. 11/369,365) with dark veins, while the male parent was 'Revolution Pinkvein', a pink-flowered commercial *petunia* plant (U.S. Plant Pat. No. 9,341) with dark veins.

The new cultivar was created in 2003 in Gilroy, Calif. and has been asexually reproduced repeatedly by vegetative cuttings and tissue culture in Gilroy, Calif. and Andijk, The Netherlands over a two-year period. The plant has also been trialed at Gilroy, Calif. and Andijk, The Netherlands. The present invention has been found to retain its distinctive characteristics through successive asexual propagations.

Plant Breeder's Rights for this cultivar were applied for in Canada on Jul. 19, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Large purple to purple-pink flowers with strong, dark violet veins;
2. Medium-green foliage with elliptical leaves;
3. A medium sized, rounded, bushy and relatively tight plant habit;
4. Moderately vigorous growth;

5. An initially low spreading to later decumbent or trailing plant habit; and
6. An early to mid-season and continuous flowering response.

DESCRIPTION OF PHOTOGRAPH

This new *petunia* plant is illustrated by the accompanying photograph which shows the overall plant habit including blooms, buds, and foliage of the plant; the colors shown are as true as can be reasonably obtained by conventional photographic procedures. The photograph is of a 3-month-old plant grown in a greenhouse in Hillscheid, Germany.

DESCRIPTION OF THE NEW CULTIVAR

The following detailed description sets forth the distinctive characteristics of 'Jam Plumein'. The data which define these characteristics were collected from asexual reproductions carried out in Hillscheid, Germany. The plant history was taken on 5 to 6-week old plants which were planted as rooted cuttings in 12-cm pots in early July 2005 and grown in a greenhouse. The plants were pinched once. Observations were made when the plants were in full flower in August 2005. Color readings were taken under natural light in the greenhouse. Color references are primarily to The R.H.S. Colour Chart of The Royal Horticultural Society of London, (R.H.S.) (2001).

DETAILED BOTANICAL DESCRIPTION

Classification:
*Family.*—Solanaceae.
*Botanical.*—*Petunia* sp.
*Common name.*—*Petunia.*

Parentage:
*Female parent.*—'Jam Bluintwo' a proprietary blue-flowered *petunia* plant (U.S. Plant patent application Ser. No. 11/369,365) with dark veins.

*Male parent.*—'Revolution Pinkvein', a commercial *petunia* plant having pink flowers (U.S. Plant Pat. No. 9,341) with dark veins.

Growth:

*Form.*—Herbaceous annual.

*Habit.*—Spreading initially, to decumbent or trailing plant habit; relatively well-branched.

*Height* (*measured from the top of the soil*).—16.2 cm.

*Width* (*horizontal plant diameter*).—23.2 cm.

*Propagation.*—Terminal tips for cutting.

*Time to produce a finished flowering plant.*—About 11 weeks for a 12-cm pot in the Spring.

*Outdoor plant performance.*—Use in hanging baskets and containers.

*Time to initiate and develop roots.*—About 25 days.

*Root description.*—Fibrous.

Stems:

*Average number* (*basal*).—6.1.

*Length of basal branches* (*from the base of the stem to the tip*).—22.7 cm.

*Internode length.*—4.8 cm.

*Diameter of branches* (*from midpoint*).—0.4 cm.

*Stem color.*—RHS 143B (green).

*Anthocyanin.*—Absent.

*Texture.*—Finely pubescent.

Leaves:

*Arrangement.*—Opposite.

*Size.*—Length: 5.7 cm. Width: 4.0 cm.

*Shape.*—Elliptical or narrowly-ovate.

*Margin.*—Entire.

*Apex.*—Acute.

*Base.*—Rounded or obtuse.

*Color.*—Upper surface: RHS 137C. Lower surface: RHS 143A to RHS 144A.

*Texture.*—Upper surface: Mainly glabrous. Lower surface: Some hair along the edge and at the veins.

*Venation.*—Mainly pinnate.

*Venation color.*—RHS 144B.

*Petioles.*—General: Very short, not clearly distinct from the leaf blade. Length: 0.1 cm to 0.3 cm. Width: 0.2 cm to 0.3 cm. Color: RHS 144 B. Texture: Densely pubescent.

Flower bud:

*Shape.*—Tube-shaped to weakly funnel-shaped with deep furrows.

*Size.*—Length: 4.5 cm. Diameter: 0.6 cm.

*Color at tight bud.*—Mainly RHS N77D (dull light-purple) or lighter.

*Immature flower color.*—RHS N78A (violet) with RHS N78D (light-violet) margin.

Inflorescence:

*Blooming habit.*—Continuous from Spring to Fall.

*Inflorescence type.*—Flowers appear solitary on pedicels, emerging singularly at the nodes.

*Number of flowers per node.*—1.

*Lastingness of individual blooms on the plant.*—7 to 9 days.

*Fragrance.*—Weak.

*Pedicels.*—Color: RHS 143B (light-green). Length: 5.1 cm. Diameter: About 0.2 cm. Texture: Densely pubescent.

Flowers:

*Shape.*—Lower part is funnel-shaped, formed by 5 fused petals; corolla margin is salver-shaped, formed by the petal lobes opening outward.

*Size.*—Diameter (flower face): 7.5 cm to 8.0 cm. Depth (total length of flower): 5.0 cm to 5.5 cm. Funnel: Length: 3.0 cm to 3.5 cm. Diameter (at opening): About 1.5 cm. Outside texture: Shallow furrows with glandular hair along the veins.

*Mature flower.*—Face/Margin Color: Upper surface: From RHS N74A (purple) near the corolla opening, fading to RHS 75A or RHS 75B (light bluish-pink) near the margin and with distinct RHS N78A (deep-purple) veins. Lower surface: Mostly RHS N74C.

*Corolla.*—Shape of corolla: Tube-shaped. Color inside (throat): RHS 79A (deep purple-violet). Color outside: RHS N77B (dull-purple).

*Petals.*—Apex: Weakly rounded, nearly truncate. Base: Fused. Margin: Entire. Waviness: Moderate. Lobation: Shallow to medium. Texture: Glabrous (upper surface).

*Calyx.*—Composed of 5 sepals fused at the base.

*Sepals.*—Number: 5. Color: Upper surface: RHS 137D. Lower surface: RHS 143A to RHS 143B. Length: Up to 1.8 cm. Width: 0.4 cm to 0.6 cm. Shape: Lanceolate. Apex: Obtuse. Base: Fused. Margin: Entire. Texture: Upper surface: Dense pubescence. Lower surface: Sparse pubescence.

Reproductive organs:

*Stamens.*—Number: 5. Filament color: RHS N155A (white). Filament length: 2.0 cm to 2.5 cm. Filament diameter: 0.1 cm. Pollen color: RHS 98D (light-blue). Pollen amount: Moderate.

*Pistil.*—Number: 1. Length: 2.5 cm. Stigma color: RHS 145A (light-green). Style color: RHS 145D (very pale-green). Style length: About 2.1 cm.

Fruit and seed set: No seed set observed so far.

Disease and insect resistance: No particular resistance or susceptibility has been observed.

COMPARISON WITH PARENTAL AND COMMERCIAL CULTIVARS

'Jam Plumein' differs from the female parent 'Jam Bluintwo' (U.S. Plant patent application Ser. No. 11/369,365) by having larger, purple to purple-pink flowers, while 'Jam Bluintwo' has light-violet flowers.

'Jam Plumein' differs from the male parent 'Revolution Pinkvein' (U.S. Plant Pat. No. 9,341) by having deeper purple to purple-pink flowers while 'Revolution Pinkvein' has pink flowers. In addition, 'Jam Plumein' has larger flowers, an earlier flowering response, and a more compact plant habit than 'Revolution Pinkvein'.

'Jam Plumein' differs from the commercial variety 'Danpethap' (U.S. publication No. 2002-0073472) by having less bluish, deeper purple flowers, while 'Danpethap' has lavender flowers. In addition, 'Jam Plumein' has better tolerance to cool temperatures than 'Danpethap'.

I claim:

1. A new and distinct cultivar of *petunia* plant as shown and described herein.

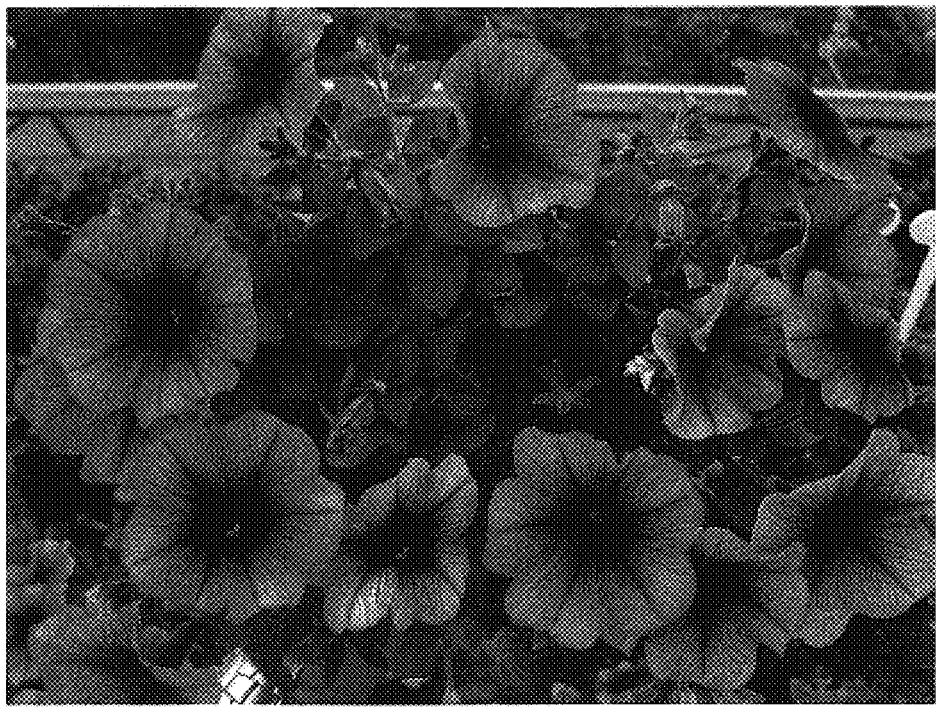

* * * * *